United States Patent [19]

Demchak et al.

[11] 4,011,062

[45] Mar. 8, 1977

[54] NOVEL COMPOSITIONS CONTAINING ACETYLENIC GLYCOL SAFENERS FOR SPRING WHEAT

[75] Inventors: Richard Joseph Demchak; David Lasilla Whitehead, both of Trenton, N.J.

[73] Assignee: American Cyanamid Company, Stamford, Conn.

[22] Filed: Sept. 9, 1975

[21] Appl. No.: 611,748

[52] U.S. Cl. .................................. 71/92; 71/86
[51] Int. Cl.² ........................................ A01N 9/22
[58] Field of Search ........................... 71/92, 122

[56] References Cited

UNITED STATES PATENTS

| | | |
|---|---|---|
| 2,997,447 | 8/1961 | Russell et al. .............. 260/635 X |
| 3,389,185 | 6/1968 | Bohm et al. .................... 71/122 X |
| 3,857,692 | 12/1974 | Feeny ............................ 71/122 X |
| 3,935,000 | 1/1976 | Fischer .......................... 71/92 X |

*Primary Examiner*—Joseph Paul Brust
*Attorney, Agent, or Firm*—Harry H. Kline

[57] ABSTRACT

Novel composition comprising in combination a 1,2-dialkyl-3,5-diphenylpyrazolium salt and an acetylenic glycol safener, and a method of utilizing said composition for the selective postemergence control of wild oats in spring wheat, whereby the said safener minimizes the phytotoxic damage frequently caused by said 1,2-dialkyl-3,5-diphenylpyrazolium salt.

12 Claims, No Drawings

NOVEL COMPOSITIONS CONTAINING ACETYLENIC GLYCOL SAFENERS FOR SPRING WHEAT

The present invention relates to a novel composition comprising, in combination, a 1,2-dialkyl-3,5-diphenylpyrazolium salt and an acetylenic glycol. More particularly, it relates to mixtures from 90% to 99%, by weight, of a 1,2-dialkyl-3,5-diphenylpyrazolium salt and from 1% to 10%, by weight, of acetylenic glycol, hereinbelow defined with particularity. Still more particularly, the invention is concerned with the aforementioned mixture which is employed as a selective postemergence control of wild oats in spring wheat with attendant minimization of phytotoxic damage to the desired crop.

It is known that substituted pyrazolium salts having the formula:

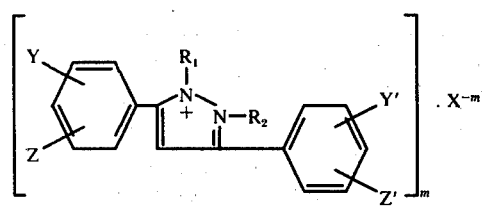

(I)

wherein $R_1$ and $R_2$ each represent lower alkyl $C_1$–$C_4$; Y, Y', Z and Z' each represent a member selected from the group consisting of hydrogen, halogen, nitro, alkyl $C_1$–$C_4$, haloalkyl $C_1$–$C_4$; m is an integer from 1 to 3; X represents an inorganic or organic anion selected from the group consisting of acetate, sulfate, hydroxide, hydrogen sulfate, methyl sulfate, benzene sulfonate, p-toluenesulfonate, nitrate, phosphate, carbonate and alkane sulfonate of $C_1$–$C_4$; are employed as herbicides in the postemergence control of wild oats (*Avena fatua*) in the presence of small grains such as wheat, barley, rye and the like. It is also known that the use of pyrazolium salts for the control of wild oats in the presence of certain spring wheat cultivars is rather limited, since certain of such cultivars are subject to some phytotoxic damage when brought in contact with these herbicides.

Considering the outstanding postemergence herbicidal activity of formula (I) pyrazolium salts in general, and that of 1,2-dimethyl-3,5-diphenylpyrazolium salts in particular for the selective control of wild oats in small grains, it is clear that the use of said pyrazolium salts for the control of wild oats in spring wheat would be of considerable advantage, provided the phytotoxic effects in spring wheat could be minimized or eliminated. To provide a composition to effect this end would meet a long felt need in the art.

Surprisingly, it has been found that certain acetylenic glycols, when employed in admixture with the above-defined pyrazolium salts for the postemergence control of wild oats in spring wheat, act as safeners or plant protective agents and will minimize or eliminate the phytotoxic damage which can result from the use of certain salts of formula (I) pyrazolium salts required to give satisfactory weed control in the above-said spring wheat cultivars. Advantageously, the acetylenic glycols which are employed as safeners in the present invention are described in U.S. Pat. No. 2,997,447 (1961). The aforementioned patent, however, does not teach or suggest the unique property of such acetylenic glycols as safeners.

In general acetylenic glycols of the present invention are generically and graphically illustrated as:

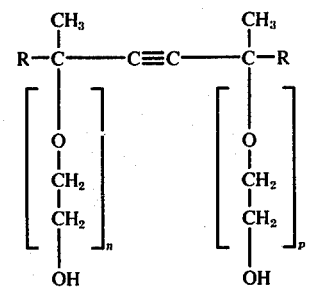

where R is ethyl or 2-methylpropyl and $n+p$ represents the number 0, 3.5, 10 or 30.

More specifically, the above acetylenic glycols can be characterized by the formula (II), (III), or (IV) as:

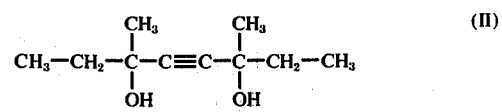

3,6-dimethyl-4-octyne-3,6-diol;

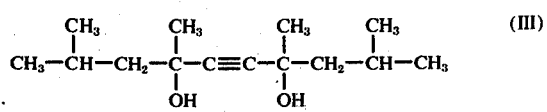

2,4,7,9-tetramethyl-5-decyne-4,7-diol; or the ethylene oxide adducts of formula (III) acetylenic glycol, represented by the formula (IV) below:

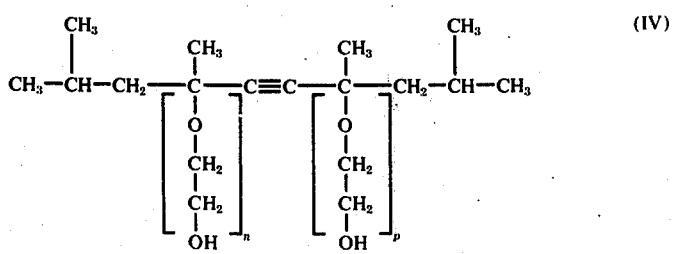

wherein the sum of $n+p$ represents 3.5, 10 or 30 moles of ethylene oxide per mole of formula (IV) adduct. Although all of the above identified acetylenic glycols protect spring wheat against phytotoxic damage caused by formula (I) pyrazolium salts, the most preferred acetylenic glycol is that of formula (III), namely 2,4,7,9-tetramethyl-5-decyne-4,7-diol.

Each of the acetylenic glycols hereinabove defined can be conveniently incorporated in herbicide formulations containing formula (I) pyrazolium salts so as to wholly or partially replace conventional surfactants normally used in said formulations. Should it be desired, the hereinabove identified plant-protective acetylenic glycols can also be added to and mixed with the dilute pyrozolium herbicide spray in situ, just prior to use.

If desired, the formula (I) pyrazolium salts can be formulated, as emulsifiable concentrates, aqueous concentrates, wettable powders and the like. Alternatively, since many of the formula (I) pyrazolium salts possess excellent solubility in water, they can be dissolved in situ, prior to use in an aqueous solution containing one of the above safeners in the desired concentration.

Formula (I) pyrazolium salts are generally used for the postemergence control of wild oats in the presence of small grains in amounts of from lb. to 4 lbs. per acre and, preferably, ½ lb. to 1½ lb. per acre of active cation.

As hereinabove stated, the acetylenic glycol safeners can be incorporated in the above herbicide formulations or added to the formula (I) pyrazolium salts in amounts ranging from about 1% to about 10%, by weight, and preferably from 1% to 5%, by weight, of formula (I). Alternatively, the acetylenic glycols of the present invention can be incorporated into the formula (I) pyrazolium salts by conventional methods, such as blending, milling, spray drying a combined herbicide-safener solution to yield homogeneous products containing the herbicides of formula I and the appropriate safener in the above-mentioned amounts.

The safeners of this invention may be admixed with the dilute aqueous spray just prior to use in amounts to provide from 0.01% to 0.5% and, preferably, 0.05% to 0.1% weight by volume of spray.

These formulations may, likewise, have added thereto an alcoholic or ketonic $C_1-C_7$ solvent, such as methanol, ethanol, n-propanol, isopropanol, methyl ketone, ethyl ketone, methyl ethyl ketone, propyl ketone or mixtures thereof.

Exemplary of such solvents are methanol, ethanol, n-propanol, isopropanol, dimethyl ketone, diethyl ketone, methyl ethyl ketone, dipropyl ketone as well as 50/50 mixtures of methanol and dimethyl ketone.

In practice it has been found that from 1.0% to 10%, by weight, of the alcohol, ketone or mixture thereof, is usually satisfactory to obtain solution of the least soluble of the acetylenic glycols.

The following non-limiting examples are set forth to further illustrate the present invention.

EXAMPLE 1

Preparation of a Water Soluble Solid Formulation Containing 1,2-Dimethyl-3,5-diphenylpyrazolium Methyl Sulfate and 2,4,7,9-Tetramethyl-5-decyne-4,7-diol as Safener 1,2-Dimethyl-3,5-diphenylpyrazolium methyl sulfate (64.8 g) and 2,4,7,9-tetramethyl-5-decyne-4,7-diol (2.7 g) are dissolved in a mixture of ethanol (10.8 g) and water (21.7 g). The resulting solution (100 g) is spray dried to afford 67.5 g of a free flowing, water soluble, powder, containing 96% by weight of 1,2-dimethyl-3,5-diphenylpyrazolium methyl sulfate and 4% by weight of 2,4,7,9-tetramethyl-5-decyne-4,7-diol.

By the above procedure, herbicide-safener mixtures are prepared containing from 91% to 99% pyrazolium salt, by weight, and of from 9% to 1%, by weight, of an acetylenic glycol safener hereinabove defined.

EXAMPLE 2

Preparation of an Aqueous Alcoholic Concentrate Formulation Containing 2 lb. per Gallon of Active Cation of 1,2-dimethyl-3,5-diphenylpyrazolium Methyl Sulfate and 2,4,7,9-Tetramethyl-5-decyne-4,7-diol as Safener 1,2-Dimethyl-3,5-diphenylpyrazolium methyl sulfate (335 g, 98% real) and 2,4,7,9-tetramethyl-5-decyne-4,7-diol (25g) are dissolved in ethanol-water (ratio 1:2 v/v) and the volume of the solution is then adjusted to 1 liter with the above ethanol-water mixture. Resultant solution is clarified by filtration.

In similar fashion, solution concentrates are made to contain from 1 to 4 lbs. per gallon of active cation of 1,2-dimethyl-3,5-diphenylpyrazolium methyl sulfate or that of another formula (I) pyrazolium salt and a formula (II), (III) or (IV) acetylenic glycol in the range of from 1 oz to 13 oz per gallon of concentrate.

EXAMPLE 3

The plant protective (safener) effect of the acetylenic glycols is demonstrated in the following test, in which postemergence control of wild oats is achieved with 1,2-dimethyl-3,5-diphenylpyrazolium methyl sulfate in the presence of certain spring wheat varieties, while the phytotoxic damage normally caused by this herbicide in the spring wheat varieties is minimized by the safener.

In the test, seedling plants are grown in jiffy flats for about 2 weeks. Test solutions are prepared from a stock solution of 1,2-dimethyl-3,5-diphenylpyrazolium methyl sulfate containing 2.10 g per liter of active cation, corresponding to 1½ lb of active cation in 86 gallon dilute aqueous spray per acre. Aliquot samples of this stock solution are diluted with aqueous solutions of the acetylenic glycols hereinabove defined in the required ratios to obtain spray solutions containing the equivalent of ¾ lb per acre of 1,2-dimethyl-3,5-diphenylpyrazolium cation in 86 gallons of aqueous spray per acre and the amount of safener (expressed as wt/vol percent concentration) and/or surfactant as indicated in Table I.

The test solutions are applied to the plants through a spray nozzle operating at 40 psi at a predetermined speed of travel to deliver the dilute aqueous spray in amounts corresponding to ¾ lb per acre of 1,2-dimethyl-3,5-diphenylpyrazolium cation. After spraying, the plants are placed on greenhouse benches and are cared for in the usual manner, commensurate with conventional greenhouse practices. Four weeks after treatment the seedling plants are examined and assigned herbitoxicity rating according to the system below. The data obtained are reported in Table I.

It can be seen from the data that a mixture of a 1,2-dimethyl-3,5-diphenylpyrazolium salt (cation) in combination with a herein defined glycol safener effectively controls wild oats in the presence of formula (I) pyrazolium salt (cation) intolerant spring wheat with attendant minimal phytotoxic damage to the latter.

This effect is especially noticable at 0.25% wt/vol. and 0.125% wt/vol. concentration of safener.

| Rating System | % Difference in Growth from Check* |
|---|---|
| 0 - No effect | 0 |
| 1 - Possible effect | 1 - 10 |
| 2 - Slight effect | 11 - 25 |
| 3 - Moderate effect | 26 - 40 |
| 5 - Definite injury | 41 - 60 |
| 6 - Herbicidal effect | 61 - 75 |
| 7 - Good herbicidal effect | 76 - 90 |
| 8 - Approaching complete kill | 91 - 99 |
| 9 - Complete kill | 100 |
| 4 - Abnormal growth; that is, a definite physiological malformation but with an overall effect less than 5. | |

*Based on visual determination of stand, size, vigor, chlorosis, growth malformation and overall plant appearance.
Plants
Wild Oats (Avena fatua)
Wheat (Triticum aestivum, cv. Lark; cv. Bonanza; cv. Waldron).

EXAMPLE 4

The experiment of Example 3 is repeated except that 1,2-dimethyl-3,5-diphenylpyrazolium methyl sulfate is applied at a rate of ½ lb per acre. Four weeks after treatment the seedling plants are examined and rated according to the rating system of Example 3. The data obtained are reported in Table II below. It can be seen from the data, that the results obtained are similar to the data obtained in Example 3 at a rate of ¾ lb per acre of herbicide.

The effect of the safener is especially noticable at 0.25% wt/vol. and 0.125% wt/vol. concentration.

Table I

Evaluation of 3,6-Dimethyl-4-octyne-3,6-diol Singly or in Combination with Conventional Surfactants as a Safener for Spring Wheat, when 1,2-Dimethyl-3,5-diphenylpyrazolium Methyl Sulfate is Used at the Rate of ¾ lb per Acre for the Postemergence Control of Wild Oats in the Presence of these Formula I Pyrazolium Compound Intolerant Crops. (Plants are Rated 4 weeks after Treatment)

| Safener, Surfactant or a Combination of Both | % wt/vol Conc. of Safener, Surfactant, or Combination in Dilute Spray | Spring Wheat Cultivars; 3-Replicates Each | | | | | | | | | Wild Oats; 3-Replicates | | |
|---|---|---|---|---|---|---|---|---|---|---|---|---|---|
| | | Lark | | | Bonanza | | | Waldron | | | | | |
| 3,6-Dimethyl-4-octyne-3,6-diol | 0.5 | 5 | 2 | 1 | 6 | 7 | 3 | 5 | 6 | 6 | 7 | 7 | 8 |
| | 0.25 | 3 | 1 | 0 | 3 | 3 | 5 | 5 | 5 | 5 | 7 | 7 | 8 |
| | 0.125 | 0 | 3 | 0 | 0 | 1 | 0 | 3 | 5 | 6 | 6 | 8 | 6 |
| Mixed Sorbitan monolaurate esters | 0.5 | 5 | 5 | 5 | 6 | 6 | 5 | 5 | 5 | 5 | 8 | 8 | 8 |
| | 0.25 | 3 | 5 | 1 | 5 | 5 | 2 | 5 | 5 | 5 | 8 | 7 | 8 |
| | 0.125 | 6 | 7 | 7 | 7 | 6 | 5 | 6 | 7 | 6 | 9 | 7 | 8 |
| Octyl phenoxy polyethoxy ethanol | 0.5 | 8 | 8 | 7 | 8 | 7 | 8 | 7 | 7 | 8 | 8 | 8 | 8 |
| | 0.25 | 5 | 7 | 6 | 5 | 7 | 6 | 6 | 7 | 5 | 8 | 8 | 8 |
| | 0.125 | 7 | 8 | 9 | 8 | 8 | 9 | 6 | 7 | 6 | 8 | 8 | 9 |
| Mixture of 3,6-Dimethyl-4-octyne-3,6-diol with mixed Sorbitan monolaurate esters | | | | | | | | | | | | | |
| Ratio 1:4 | 0.5 | 6 | 7 | 7 | 8 | 9 | 7 | 6 | 6 | 7 | 8 | 8 | 9 |
| 2:3 | 0.5 | 7 | 8 | 8 | 7 | 8 | 7 | 7 | 7 | 7 | 8 | 8 | 8 |
| 3:2 | 0.5 | 5 | 3 | 2 | 5 | 6 | 3 | 5 | 5 | 5 | 8 | 8 | 8 |
| Mixture of 3,6-Dimethyl-4-octyne-3,6-diol with octylphenoxy polyethoxy ethanol | | | | | | | | | | | | | |
| Ratio 1:4 | 0.5 | 7 | 8 | 8 | 8 | 9 | 7 | 7 | 7 | 7 | 8 | 8 | 9 |
| 2:3 | 0.5 | 9 | 8 | 9 | 9 | 9 | 9 | 7 | 8 | 7 | 9 | 9 | 9 |
| 3:2 | 0.5 | 7 | 8 | 8 | 8 | 8 | 7 | 7 | 7 | 6 | 8 | 8 | 8 |
| Alkylarylpolyoxyethylene glycols mixed with free fatty acids | 0.5 | 6 | 7 | 5 | 7 | 7 | 7 | 5 | 5 | 3 | 9 | 8 | 9 |

Table II

Evaluation of 3,6-Dimethyl-4-octyne-3,6-diol Singly or in Combination with Conventional Surfactants as a Safener for Spring Wheat, when 1,2-Dimethyl-3,5-diphenylpyrazolium Methyl Sulfate is used at the Rate of ½ lb per Acre for the Postemergence Control of Wild Oats in the Presence of these Formula I Pyrazolium Compound Intolerant Crops (Plants are rated 4 Weeks after Treatment)

| Safener, Surfactant or a Combination of Both | % wt/vol Conc. of Safener, Surfactant, or Combination in Dilute Spray | Spring Wheat Cultivars; 3-Replicates Each | | | | | | | | | Wild Oats; 3-Replicates | | |
|---|---|---|---|---|---|---|---|---|---|---|---|---|---|
| | | Lark | | | Bonanza | | | Waldron | | | | | |
| 3,6-Dimethyl-4-octyne-3,6-diol | 0.5 | 0 | 0 | 0 | 0 | 6 | 0 | 2 | 3 | 0 | 3 | 5 | 2 |
| | 0.25 | 2 | 0 | 0 | 0 | 5 | 0 | 2 | 3 | 0 | 6 | 7 | 6 |
| | 0.125 | 0 | 0 | 0 | 0 | 0 | 0 | 0 | 3 | 0 | 7 | 7 | 3 |
| Mixed Sorbitan monolaurate esters | 0.5 | 1 | 2 | 0 | 3 | 3 | 2 | 5 | 5 | 2 | 7 | 7 | 7 |
| | 0.25 | 0 | 3 | 3 | 2 | 3 | 1 | 3 | 5 | 5 | 7 | 7 | 8 |
| | 0.125 | 1 | 2 | 0 | 1 | 3 | 0 | 3 | 3 | 3 | 7 | 7 | 7 |
| Octylphenxoy polyethoxy ethanol | 0.5 | 7 | 8 | 7 | 7 | 7 | 6 | 7 | 6 | 5 | 9 | 8 | 8 |
| | 0.25 | 5 | 7 | 6 | 5 | 5 | 5 | 5 | 5 | 3 | 9 | 7 | 8 |
| | 0.125 | 5 | 5 | 3 | 5 | 5 | 3 | 3 | 5 | 3 | 7 | 7 | 9 |
| 3,6-Dimethyl-4-octyne-3,6-diol mix with | | | | | | | | | | | | | |

Table II-continued

Evaluation of 3,6-Dimethyl-4-octyne-3,6-diol Singly or in Combination with Conventional Surfactants as a Safener for Spring Wheat, when 1,2-Dimethyl-3,5-diphenylpyrazolium Methyl Sulfate is used at the Rate of ½ lb per Acre for the Postemergence Control of Wild Oats in the Presence of these Formula I Pyrazolium Compound Intolerant Crops (Plants are rated 4 Weeks after Treatment)

| Safener, Surfactant or a Combination of Both | % wt/vol Conc. of Safener, Surfactant, or Combination in Dilute Spray | Spring Wheat Cultivars; 3-Replicates Each | | | | | | | | Wild Oats; 3-Replicates | | |
|---|---|---|---|---|---|---|---|---|---|---|---|---|
| | | Lark | | | Bonanza | | | Waldron | | | | |
| Sorbitan monolaurate esters | | | | | | | | | | | | |
| Ratio 1:4 | 0.5 | 1 | 3 | 3 | 2 | 3 | 6 | 3 | 5 | 3 | 7 | 7 | 7 |
| 2:3 | 0.5 | 2 | 5 | 3 | 2 | 6 | 6 | 3 | 5 | 2 | 7 | 7 | 7 |
| 3:2 | 0.5 | 2 | 3 | 1 | 5 | 6 | 2 | 5 | 3 | 3 | 9 | 7 | 7 |
| 3,6-Dimethyl-4-octyne-3,6-diol, mix with octylphenoxy polyethoxy ethanol | | | | | | | | | | | | | |
| Ratio 1:4 | 0.5 | 7 | 7 | 8 | 7 | 7 | 7 | 6 | 6 | 5 | 8 | 7 | 9 |
| 2:3 | 0.5 | 7 | 9 | 7 | 8 | 9 | 8 | 7 | 7 | 6 | 8 | 8 | 8 |
| 3:2 | 0.5 | 7 | 7 | 7 | 8 | 7 | 7 | 5 | 7 | 7 | 8 | 8 | 8 |
| Alkylarylpolyoxyethylene glycols mixed with free fatty acids | 0.5 | 5 | 6 | 5 | 5 | 6 | 3 | 5 | 5 | 5 | 8 | 7 | 8 |

EXAMPLE 5

Repeating the procedure of Example 3, the plant protective (safener) effects of 2,4,7,9-tetramethyl-5-decyne-4,7-diol and the formula (IV) ethylene oxide adducts are evaluated in conjunction with ¾ lb per acre of 1,2-dimethyl-3,5-diphenylpyrazolium cation (as the methyl sulfate salt) for the control of wild oats in the presence of spring wheat, and are compared to a formulation containing the above herbicide and a conventional surfactant. Five weeks after treatment the seedling plants are examined and rated according to the rating system of Example 3. The data obtained are recorded in Table III.

It can be seen from the data that the acetylenic glycols reduce the phytotoxic damage in formula (I) pyrazolium compound intolerant spring wheat. This effect is especially noticable at 0.125% wt/vol. and 0.063% wt/vol. concentration of safener.

Table III

Evaluation of Acetylenic Glycols as Safeners for the Protection of Spring Wheat against Phytotoxic Damage caused by 1,2-Dimethyl-3,5-diphenylpyrazolium Methyl Sulfate Applied at a Rate of ¾ lb per Acre Active Cation for the Postemergence Control of Wild Oats (Plants Rated 5 Weeks after Application)

| Safener, Surfactant or a Combination of Both | % wt/vol Conc. of Safener, Surfactant, or Combination in Dilute Spray | Spring Wheat Cultivars; 3-Replicates each | | | | | | Wild Oats; 3-Replicates | | |
|---|---|---|---|---|---|---|---|---|---|---|
| | | Bonanza | | | Waldron | | | | | |
| Octylphenoxy polyethoxy ethanol | 0.5 | 7 | 7 | 3 | 5 | 7 | 7 | 7 | 7 | 7 |
| | 0.125 | 3 | 5 | 5 | 5 | 6 | 5 | 8 | 7 | 9 |
| | 0.063 | 6 | 5 | 7 | 6 | 9 | 7 | 9 | 9 | 9 |
| Formula IV Adduct (10 moles of ethylene oxide) | 0.5 | 2 | 6 | 5 | 3 | 5 | 1 | 7 | 7 | 6 |
| | 0.125 | 1 | 2 | 2 | 3 | 3 | 3 | 8 | 9 | 9 |
| | 0.063 | 1 | 2 | 3 | 5 | 7 | 2 | 8 | 9 | 8 |
| Formula IV Adduct (30 moles of ethylene oxide) | 0.5 | 2 | 2 | 5 | 6 | 5 | 2 | 8 | 9 | 9 |
| | 0.125 | 0 | 0 | 5 | 2 | 3 | 3 | 6 | 8 | 9 |
| | 0.063 | 0 | 0 | 2 | 3 | 5 | 6 | 8 | 8 | 9 |
| 2,4,7,9-Tetramethyl-5-decyne-4,7-diol | 0.063 | 0 | 3 | 6 | 1 | 1 | 2 | 9 | 9 | 9 |
| 2,4,7,9-Tetramethyl-5-decyne-4,7-diol + Octylphenoxy polyethoxy ethanol | 0.063 + 0.063 | 7 | 9 | 7 | 7 | 6 | 6 | 8 | 9 | 8 |

EXAMPLE 6

The procedure of Example 5 is repeated except that 1,2-dimethyl-3,5-diphenylpyrazolium methyl sulfate is applied at a rate of ½ lb per acre of active cation. Five weeks after treatment the seedling plants are examined and rated as in Example 5. The data obtained are recorded in Table IV.

It can be seen from the data that acetylenic glycols of the present invention reduce phytotoxic damage in formula I pyrazolium compound intolerant spring wheat.

This effect is especially noticable at 0.125% wt/vol. and 0.063% wt/vol. concentration of safener.

TABLE IV

Evaluation of Acetylenic Glycols as Safeners for the Protection of Spring Wheat Against Phytotoxic Damage caused by 1,2-Dimethyl-3,5-diphenylpyrazolium Methyl Sulfate Applied at a Rate of ½ lb per Acre Active Cation for the Postemergence Control of Wild Oats (Plants Rated 5 Weeks after Application)

| Safener, Surfactant or a Combination of Both | % wt/vol Conc. of Safener, Surfactant, or Combination in Dilute Spray | Spring Wheat Cultivars; 3-Replicates each Bonanza | | | Waldron | | | Wild Oats; 3-Replicates | | |
|---|---|---|---|---|---|---|---|---|---|---|
| Octylphenoxy Polyethoxy ethanol | 0.5 | 2 | 7 | 6 | 2 | 7 | 6 | 9 | 8 | 8 |
| | 0.125 | 2 | 2 | 3 | 3 | 1 | 2 | 7 | 9 | 8 |
| | 0.063 | 7 | 8 | 8 | 6 | 5 | 3 | 9 | 8 | 9 |
| Formula IV Adduct (10 moles of ethylene oxide) | 0.5 | 2 | 2 | 2 | 3 | 3 | 2 | 7 | 8 | 8 |
| | 0.125 | 3 | 1 | 2 | 1 | 1 | 2 | 7 | 9 | 9 |
| | 0.063 | 1 | 2 | 3 | 1 | 2 | 3 | 8 | 8 | 7 |
| Formula IV Adduct (30 moles of ethylene oxide) | 0.5 | 2 | 5 | 6 | 6 | 5 | 6 | 8 | 9 | 9 |
| | 0.125 | 0 | 1 | 2 | 0 | 2 | 0 | 8 | 9 | 6 |
| | 0.063 | 0 | 2 | 2 | 1 | 1 | 1 | 8 | 9 | 7 |
| 2,4,7,9-Tetramethyl-5-decyne-4,7-diol | 0.063 | 0 | 0 | 0 | 2 | 2 | 3 | 8 | 8 | 7 |
| 2,4,7,9-Tetramethyl-5-decyne-4,7-diol + Octylphenoxy polyethoxy ethanol | 0.063 + 0.063 | 6 | 9 | 6 | 3 | 8 | 7 | 7 | 8 | 7 |

EXAMPLE 7

Table V

Evaluation of 3,6-Dimethyl-4-octyne-3,6-diol as Safener, used in Combination with Mixed Sorbitan Monolaurates (Surfactant) for the Protection of Spring Wheat against Phytotoxic Damage caused by 1,2-Dimethyl-3,5-diphenylpyrazolium Methyl Sulfate Applied at ¾ lb per Acre of Active Cation for the Postemergence Control of Wild Oats (Plants are Rated 5 Weeks after Application)

| Safener, Surfactant or Combination | % wt/vol Conc. of Safener, Surfactant, or Combination in Dilute Spray | Spring Wheat Cultivars; 3-Replicates Each Lark | | | Waldron | | | Wild Oats; 3-Replicates | | |
|---|---|---|---|---|---|---|---|---|---|---|
| 3,6-Dimethyl-4-octyne-3,6-diol in Combination with Mixed Sorbitan Monolaurates Ratio 3:2 | 0.5 | 0 | 9 | 3 | 3 | 8 | 9 | 9 | 9 | 9 |
| | 0.25 | 0 | 2 | 3 | 3 | 5 | 5 | 9 | 9 | 9 |
| | 0.125 | 0 | 0 | 0 | 0 | 2 | 2 | 8 | 9 | 8 |

By the procedure of Example 3 the combination of 3,6-dimethyl-4-octyne-3,6-diol with mixed sorbitan monolaurate surfactant in a 3:2 ratio is evaluated as a safener for the protection of 1,2-dimethyl-3,5-diphenylpyrazolium methyl sulfate intolerant spring wheat, when this herbicide is applied at a rate of ¾ lb per acre active cation for the postemergence control of wild oats. Five weeks after treatment the seedling plants are examined and rated according to the rating system of Example 3. The data obtained are recorded in Table V below.

EXAMPLE 8

The procedure of Example 7 is repeated, except 1,2-dimethyl-3,5-diphenylpyrazolium methyl sulfate is applied at a rate of ½ lb per acre of active cation. Five weeks after treatment the seedling plants are examined and rated as in Example 7. The data obtained are recorded in Table VI below.

Table VI

Evaluation of 3,6-Dimethyl-4-octyne-3,6-diol as Safener, used in Combination with Mixed Sorbitan Monolaurates (Surfactant) for the Protection of Spring Wheat against Phytotoxic Damage caused by 1,2-Dimethyl-3,5-diphenylpyrazolium Methyl Sulfate Applied at ½ lb per Acre of Active Cation for the Postemergence Control of Wild Oats (Plants are Rated 5 Weeks after Application)

| Safener, Surfactant or Combination | % wt/vol Conc. of Safener, Surfactant, or Combination in Dilute Spray | Spring Wheat Cultivars; 3-Replicates Each Lark | | | Waldron | | | Wild Oats; 3-Replicates | | |
|---|---|---|---|---|---|---|---|---|---|---|
| 3,6-Dimethyl-4-octyne-3,6-diol in Combination with Mixed Sorbitan monolaurates Ratio 3:2 | 0.5 | 0 | 0 | 0 | 2 | 3 | 2 | 9 | 9 | 8 |
| | 0.25 | 0 | 0 | 0 | 0 | 2 | 2 | 8 | 8 | 7 |
| | 0.125 | 0 | 0 | 0 | 0 | 0 | 0 | 7 | 9 | 6 |

We claim:

1. A composition of matter comprising: a mixture of from about 90% to about 99%, by weight, of a compound having the formula (I):

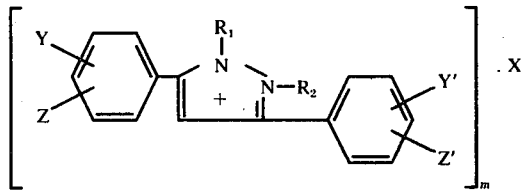

wherein $R_1$ and $R_2$ are each lower alkyl $C_1$–$C_4$; Y,Y',Z and Z' are members selected from the group consisting of hydrogen, halogen, nitro, alkyl $C_1$–$C_4$, haloalkyl $C_1$–$C_4$, alkoxy $C_1$–$C_4$, m is an integer from 1 to 3; X is an anion selected from the group consisting of acetate, sulfate, hydroxide, hydrogen sulfate, methyl sulfate, benzene sulfonate, p-toluenesulfonate, nitrate, phosphate, carbonate and alkane sulfonate $C_1$–$C_4$; and from about 1% to about 10%, by weight, of a compound having the formula:

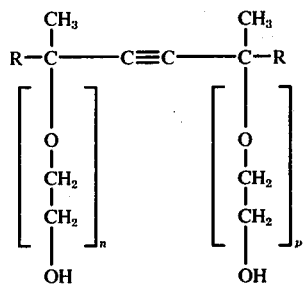

wherein R is selected from the group consisting of ethyl and 2-methylpropyl; and $n+p$ represents the number 0, 3.5, 10 or 30.

2. The composition of matter according to claim 1, wherein R is 2-methylpropyl; $n+p$ is 0; $R_1$ and $R_2$ are both methyl and Y,Y',Z and Z' are hydrogen.

3. The composition of matter according to claim 1, wherein R is ethyl; $n+p$ is 0; $R_1$ and $R_2$ are both methyl; Y,Y',Z and Z' are hydrogen.

4. The composition of matter according to claim 1, wherein the mixture comprises 1,2-dimethyl-3,5-diphenyl-pyrazolium methyl sulfate and 2,4,7,9-tetramethyl-5-decyne-4,7-diol.

5. The composition of matter according to claim 1, wherein the mixture comprises: 1,2-dimethyl-3,5-diphenyl-pyrazolium methyl sulfate and 3,6-dimethyl-4-octyne-3,6-diol.

6. The composition of matter comprising: a mixture of from 1 lb to 4 lb by weight of active cation per gallon of aqueous solution of a compound having the claim 1 formula (I):

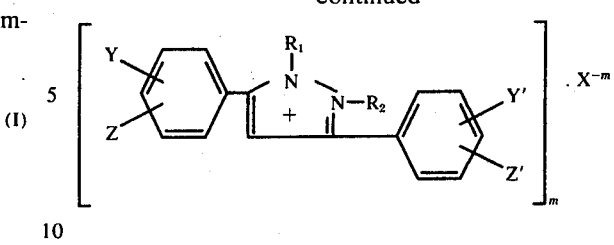

wherein $R_1$ and $R_2$ each are selected from lower alkyl $C_1$–$C_4$; Y,Y',Z and Z' are members selected from the group consisting of hydrogen, halogen, nitro, alkyl $C_1$–$C_4$, haloalkyl $C_1$–$C_4$, alkoxy $C_1$–$C_4$; m is an integer from 1 to 3; X is an anion selected from the group consisting of acetate, sulfate, hydroxide, hydrogen sulfate, methyl sulfate, benzene sulfonate, p-toluenesulfonate, nitrate, phosphate, carbonate and alkane sulfonate $C_1$–$C_4$;

from 1 oz to 13 oz. by weight per gallon solution of a compound having the formula:

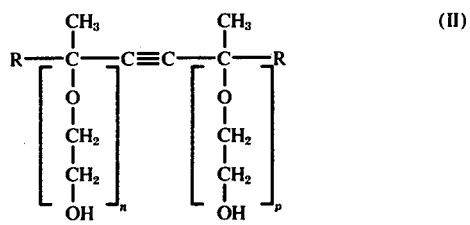

wherein R is a member selected from the group consisting of ethyl and 2-methylpropyl; $n+p$ represents the number 0, 3.5, 10 or 30; and from 1% to 10% by weight of a solvent selected from the group consisting of water, lower alcohol $C_1$–$C_3$, lower ketone $C_1$–$C_3$, and mixture thereof in the amount so as to obtain 1 gallon solution of a mixture containing from 1 lb to 4 lb by weight of active cation of formula (I) compound and from 1 oz to 13 oz by weight of formula (II) compound.

7. The composition of matter according to claim 6, wherein said formula I compound is 1,2-dimethyl-3,5-diphenyl-pyrazolium methyl sulfate and said formula (II) compound is 2,4,7,9-tetramethyl-5-decyne-4,7-diol.

8. The composition of matter according to claim 6, wherein said formula I compound is 1,2-dimethyl-3,5-diphenyl-pyrazolium methyl sulfate and said formula (II) compound is 3,6-dimethyl-4-octyne-3,6-diol.

9. A method for the control of wild oats in the presence of spring wheat comprising: contacting said weed with a herbicidally effective amount of a mixture of from about 90% to about 99%, by weight, of a compound having the formula (I):

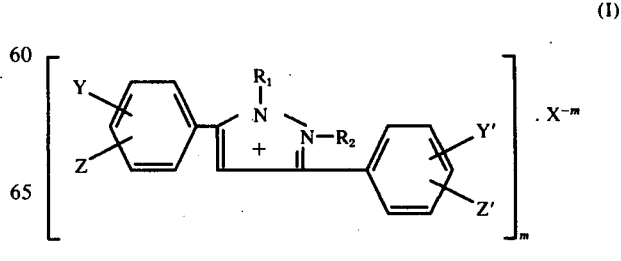

wherein $R_1$ and $R_2$ are each lower alkyl $C_1$-$C_4$; Y,Y',Z and Z' are members selected from the group consisting of hydrogen, halogen, nitro, alkyl $C_1$-$C_4$, haloalkyl $C_1$-$C_4$, alkoxy $C_1$-$C_4$; m is an integer selected from 1,2 and 3; X is an anion selected from the group consisting of acetate, sulfate, hydroxide, hydrogen sulfate, methyl sulfate, benzene sulfonate, p-toluenesulfonate, nitrate, phosphate, carbonate and alkane sulfonate $C_1$-$C_4$; and containing 1% to 10% by weight of a compound having the formula:

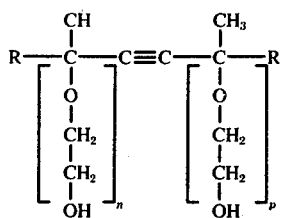  (II)

wherein R is selected from the group consisting of ethyl and 2-methylpropyl; $n+p$ represents the number 0, 3.5, 10 or 30.

10. The method according to claim 9, wherein said mixture comprises 1,2-dimethyl-3,5-diphenyl-pyrazolium methyl sulfate and 2,4,7,9-tetramethyl-5-decyne-4,7-diol.

11. The method according to claim 9, wherein said mixture comprises 1,2-dimethyl-3,5-diphenyl-pyrazolium methyl sulfate and 3,6-dimethyl-4-octyne-3,6-diol.

12. The method according to claim 9, wherein said mixture contains ½ lb to 1½ lb per acre of the pyrazolium cation of the formula (I) of claim 9 and 1 oz to 8 oz per acre of the acetylenic glycol of the formula (II) of claim 9.

* * * * *